(12) United States Patent
Valia et al.

(10) Patent No.: US 9,186,352 B2
(45) Date of Patent: Nov. 17, 2015

(54) CHEMICAL COMPOSITIONS FOR ENHANCING TRANSDERMAL DELIVERY OF THERAPEUTIC AGENTS

(71) Applicant: InteguRx Therapeutics, LLC, Califon, NJ (US)

(72) Inventors: Kirti H. Valia, Plainsboro, NJ (US); Agis Kydonieus, Kendall Park, NJ (US)

(73) Assignee: InteguRx Therapeutics, LLC, Califon, NJ (US)

( * ) Notice: Subject to any disclaimer, the term of this patent is extended or adjusted under 35 U.S.C. 154(b) by 0 days.

(21) Appl. No.: 14/168,571

(22) Filed: Jan. 30, 2014

(65) Prior Publication Data

US 2014/0148491 A1    May 29, 2014

Related U.S. Application Data

(63) Continuation of application No. PCT/US2013/056391, filed on Aug. 23, 2013.

(60) Provisional application No. 61/693,135, filed on Aug. 24, 2012, provisional application No. 61/777,276, filed on Mar. 12, 2013.

(51) Int. Cl.
*A61K 31/4178* (2006.01)
*A61K 9/00* (2006.01)
*A61K 47/12* (2006.01)
*A61K 9/08* (2006.01)
*A61K 31/439* (2006.01)
*A61K 31/46* (2006.01)
*A61K 31/4709* (2006.01)

(52) U.S. Cl.
CPC ........... *A61K 31/4178* (2013.01); *A61K 9/0014* (2013.01); *A61K 9/08* (2013.01); *A61K 31/439* (2013.01); *A61K 31/46* (2013.01); *A61K 31/4709* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 6,264,980 B1 * | 7/2001 | Hille | 424/449 |
| 6,383,471 B1 | 5/2002 | Chen et al. | |
| 7,879,344 B2 | 2/2011 | Feldkamp et al. | |
| 8,623,387 B2 | 1/2014 | Yamaguchi et al. | |
| 2005/0002997 A1 * | 1/2005 | Howard et al. | 424/449 |
| 2005/0266060 A1 | 12/2005 | Bruinsma | |
| 2006/0198881 A1 * | 9/2006 | Howard et al. | 424/449 |
| 2007/0264319 A1 * | 11/2007 | Lebo et al. | 424/449 |
| 2008/0200533 A1 | 8/2008 | Krishnan | |
| 2008/0319092 A1 | 12/2008 | Singh | |
| 2009/0098069 A1 | 4/2009 | Vacca | |
| 2010/0119585 A1 | 5/2010 | Hille et al. | |

FOREIGN PATENT DOCUMENTS

| | | | | |
|---|---|---|---|---|
| EP | 2266626 | 12/2010 | | |
| JP | 2003/160489 | 6/2003 | | |
| WO | WO 93/03767 | 4/1993 | | |
| WO | WO 96/22083 | * 7/1996 | | A61K 9/70 |
| WO | WO 00/47208 | 8/2000 | | |
| WO | WO 03/013482 | 2/2003 | | |
| WO | WO 2005/032514 | 4/2005 | | |

OTHER PUBLICATIONS

Gwak, et al., Drug Development and Industrial Pharmacy, vol. 30, No. 2, pp. 187-194, 2004.*
Lavafer, Robert H. USP reference Standards at http://www.usp.org/reference-standards, copyright 2015.*
Paudel et al., "Challenges and opportunities in dermal/transdermal delivery", Ther. Deliv., Jul. 1, 2010, 1, 109-131.
Gwak et al., "Transdermal Delivery of Ondansetron Hydrochloride: Effects of Vehicles and Penetration Enhancers", Drug Dev. and Industrial Pharm., 2004, 30(2): 187-194.
Jenner et al, "Transdermal delivery of physostigmine. A pretreatment against organophosphate poisoning", J. Pharm Pharmacol., 1995, 47(3), 206-212.
Kydonieus et al., "Transdermal Delivery Device Development: A Patent Review", 2006, 17 pages.
Takahashi et al., "Novel Approach to Improve Permeation of Ondansetron Across Shed Snake Skin as a Model Membrane", J. Pharm Pharmacol., 2001; 53(6):789-794.
Williams et al., "Penetration Enhancers", Advanced Drug Delivery Reviews, 2004, 56, 603-618.

* cited by examiner

*Primary Examiner* — Alicia L Otton
*Assistant Examiner* — JeanMarie Calvillo
(74) *Attorney, Agent, or Firm* — Baker & Hostetler LLP

(57) ABSTRACT

The present application discloses chemical compositions and methods for enhancing the transdermal permeation of therapeutic agents through skin. The chemical compositions and methods of the invention can include combinations of a first fatty acid having about 14 or more carbon atoms and a second fatty acid having about 10 or less carbon atoms. These compositions are useful for the delivery of therapeutic agents, in particular hard to deliver drugs such as those that have fused rings, including ondansetron, and large drugs such as peptides. The compositions of the invention can be formulated as transdermal gels, lotions, creams, transdermal patches, sprays or mists.

11 Claims, 12 Drawing Sheets

CHEMICAL COMPOSITIONS FOR ENHANCING TRANSDERMAL DELIVERY OF THERAPEUTIC AGENTS

CROSS-REFERENCE TO RELATED PATENT APPLICATIONS

This application is continuation-in-part of International Application No. PCT/US2013/056391, filed Aug. 23, 2013, which claims priority to U.S. Pat. App. No. 61/693,135 filed Aug. 24, 2012 and U.S. Pat. App. No. 61/777,276 filed Mar. 12, 2013, the entireties of which are incorporated by reference herein for all purposes.

TECHNICAL FIELD

The present disclosure relates generally to the field of transdermal delivery of therapeutic agents. More specifically, the present disclosure relates to chemical compositions and methods used to enhance the transdermal permeation of therapeutic agents.

BACKGROUND

Fatty acids are known as chemical enhancers in the field of transdermal delivery. Various fatty acids have been used to enhance the delivery of several drugs. The list of fatty acids used is extensive and encompasses saturated fatty acids such as capric acid, unsaturated fatty acids such as linoleic acid, and branched fatty acids C6 to C18, such as isostearic acid. Hydroxy fatty acids such as 2-hydroxyoctanoic acid are known to plasticize the skin, but they have not been explored for their effect on the skin permeation of drugs.

The effect of the different fatty acids on the permeation of drugs through skin is not well understood and it depends upon the vehicle, the drug used and the structure and concentration of the fatty acid. For example, oleic acid has been used to increase the permeability of acyclovir, tetrahydrocannabinol, mannitol and dihydroergotamine. Laurie acid has been used to increase the permeation of naloxone, dihydroergotamine and leuprolide. The enhancement ratio for naloxone's skin permeation using lauric acid as the enhancer were 150, 25, 15, 10 and 3 when the vehicle was propylene glycol, PEG 400, mineral oil, isopropanol and isopropyl myristate respectively. What is significant from the above references is the fact that the fatty acids increased the skin permeability by orders of magnitude for some drugs, whereas under similar experimental conditions the skin permeation of other compounds was not affected much at all. This supports the understanding that chemical enhancement is still more of an art than science. Therefore, the enhancement cannot be predicted from the properties of the drug and the fatty acid or that of the vehicle.

In general the skin permeation enhancement by saturated fatty acids is best for C10 and C12 fatty acids. C18 unsaturated fatty acids appear to be better than saturated ones but it is not clear that the same relationship is true for medium and low molecular weight fatty acids. In the studies trying to determine the effect of branching on skin permeation no difference was observed between branched and linear fatty acids except on some occasions. Increase in the concentration of the fatty acid in the formulation did not show a linear response either.

However, concentrations between 2 and 10% can be used to increase permeation and also to limit the skin irritation that can be caused by fatty acids.

It has now been found that the compositions of two fatty acids having different molecular weights of the present invention have a synergistic effect and increase the transdermal permeation of therapeutic agents to a surprising degree.

SUMMARY

Various embodiments of a composition to enhance the transdermal permeation of a therapeutic agent are disclosed. In one embodiment the composition comprises a first fatty acid, or derivative or congener thereof, comprising about 14 or more carbon atoms and a second fatty acid, or derivative or congener thereof, comprising about 10 or less carbon atoms.

In another embodiment the composition comprises a first fatty acid and a second fatty acid, wherein the first and second fatty acids comprise a different number of carbon atoms. The composition can include a first fatty acid comprising about 14 or more carbon atoms and a second fatty acid comprising about 12 or less carbon atoms.

In another embodiment the composition comprises a first fatty acid, or derivative or congener thereof, a second fatty acid, or derivative or congener thereof, and a therapeutic agent, wherein the first fatty acid comprises about 14 or more carbon atoms and the second fatty acid comprises about 10 or less carbon atoms.

Methods for treating a patient in need thereof are also disclosed. In one embodiment the method for treating a patient in need thereof comprises administering to a patient's skin a composition comprising a first fatty acid, or derivative or congener thereof, a second fatty acid, or derivative or congener thereof, and a therapeutic agent, wherein the first fatty acid comprises about 14 or more carbon atoms and the second fatty acid comprises about 10 or less carbon atoms.

In one embodiment the method for treating a patient in need thereof comprises administering to a patient's skin a composition comprising a first fatty acid, a second fatty acid, and a therapeutic agent, wherein the first fatty acid comprises about 14 or more carbon atoms and the second fatty acid comprises about 12 or less carbon atoms.

Methods for use of a composition are also disclosed. In one embodiment the use of a composition comprising a first fatty acid, or derivative or congener thereof, a second fatty acid, or derivative or congener thereof, and a therapeutic agent comprises the manufacture of a medicament for treating a disease or condition, wherein the first fatty acid comprises about 14 or more carbon atoms and the second fatty acid comprises about 10 or less carbon atoms.

In one embodiment the use of a composition comprising a first fatty acid, a second fatty acid, and a therapeutic agent comprises the manufacture of a medicament for treating a disease or condition, wherein the first fatty acid comprises about 14 or more carbon atoms and the second fatty acid comprises about 12 or less carbon atoms.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
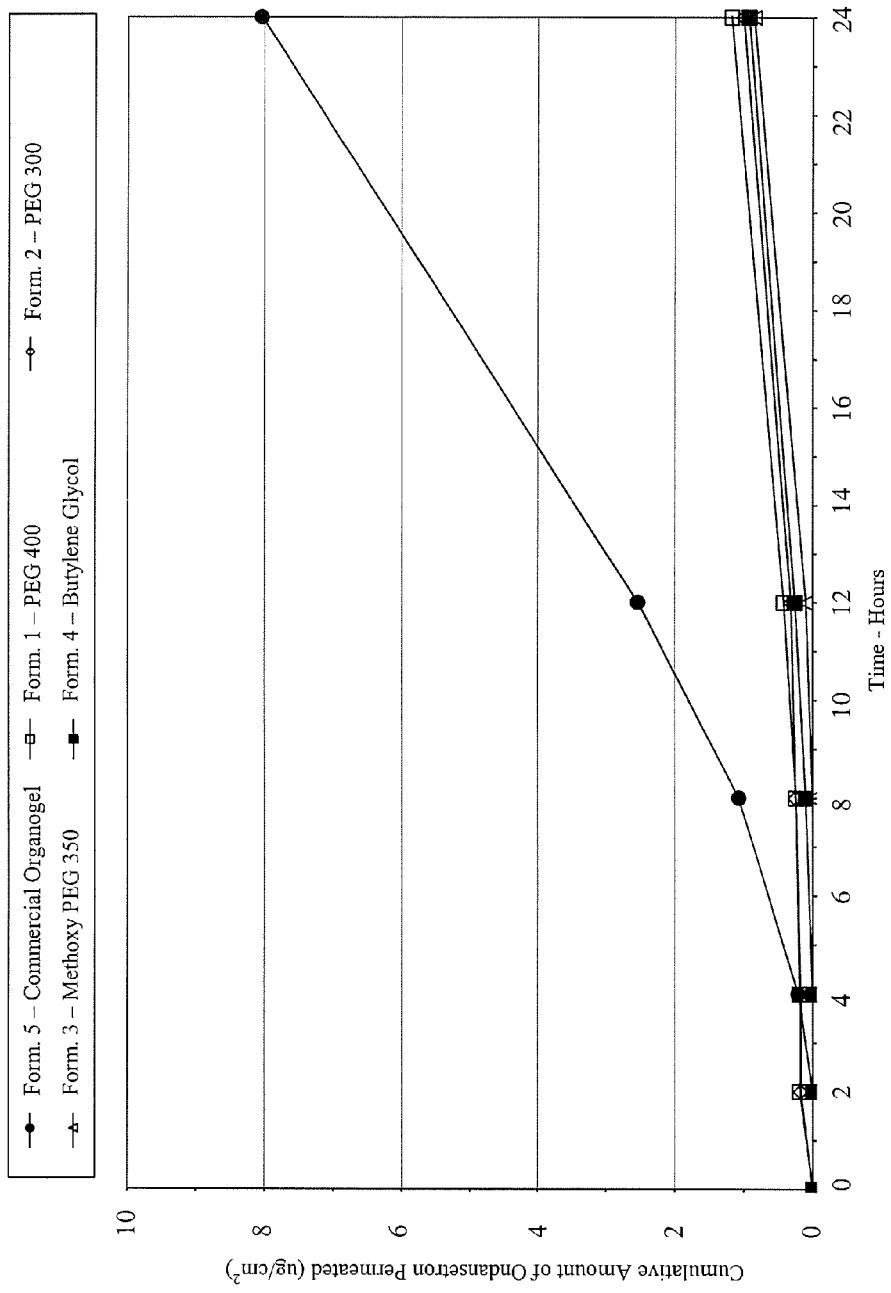
FIG. 1 illustrates average cumulative amount of ondansetron base that permeated through human skin over a 24 hour period without the benefit of the present invention.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

It has now been observed that when two fatty acids of different molecular weights are used together as a composition for enhancing transdermal permeation of a drug or biologic, the permeation through human skin is increased by orders of magnitude more than when each of the fatty acids is used alone. Surprisingly, when a composition including a low molecular weight fatty acid and a high molecular weight fatty acid is used in combination with a drug, there is an extremely high increase in transdermal permeation of the drug.

In particular, and as further demonstrated in the examples, when oleic acid and levulinic acid are used together, at the same concentration as when oleic acid or levulinic acid is used separately, the cumulative amount of the ondansetron that permeated through human skin increased a) 450-fold over the unenhanced formulation, b) 255-fold over the formulation containing only levulinic acid, c) 32-fold over a commercially available ondansetron organogel and d) 9-fold over the formulation containing only oleic acid.

Without limiting the invention to a particular mechanism of action, it can now be hypothesized that the low molecular weight fatty acids permeate into the lipid bilayers of the skin and rapidly plasticize them. This allows for the larger lipids to penetrate into the bilayers much more easily and in larger quantities and thus disrupt the ordered structure of intercellular bilayers, thus allowing greater drug permeation.

In accordance with an aspect of the present invention, there are provided compositions that include a combination of two or more fatty acids having different molecular weights. These compositions are useful for enhancing the transdermal permeation of a therapeutic agent. In particular, the invention provides for the use of a combination enhancing system comprising a low molecular weight fatty acid and a higher molecular weight fatty acid to increase the transdermal permeation of difficult-to-deliver drugs and biologics. The high molecular weight fatty acid and low molecular weight fatty acids may be characterized by the number of carbon atoms present in the hydrocarbon chain of the fatty acid. Ondansetron is one such drug that has enhanced transdermal permeation when delivered in accordance with compositions or methods of the invention.

As used herein, the term "transdermal permeation" includes both percutaneous delivery and transmucosal delivery, that is, passage through skin or mucosal tissue and into the bloodstream.

As used herein in reference to transdermal penetration, the term "enhancing" refers to increasing the rate at which a therapeutic agent penetrates the skin or mucosal tissue and enters the bloodstream.

As used herein, the term "fatty acid" has its ordinary meaning as would be understood by a person of ordinary skill in the art and includes a molecule having a carboxylic group and a hydrocarbon chain. Descriptions of the number of carbon atoms in a fatty acid herein refer to the number of carbon atoms in the hydrocarbon chain of the fatty acid, irrespective of whether the hydrocarbon chain is straight or branched.

As used herein, the term "fatty acid" includes saturated fatty acids, which do not contain any double or triple bonds in the hydrocarbon chain. Saturated fatty acids include, but are not limited to propionic acid (C3) (by way of example, C3 indicates propionic acid has 3 carbon atoms in its hydrocarbon chain; the number of carbon atoms in the hydrocarbon chain of other example fatty acids is denoted in analogous fashion herein), butyric acid (C4), valeric acid (C5), caproic acid (C6), enanthic acid (C7), caprylic acid (C8), pelargonic acid (C9), capric acid (C10), undecylic acid (C11), lauric acid (C12), tridecylic acid (C13), myristic acid (C14), pentadecylic acid (C15), palmitic acid (C16), margaric acid (C17), stearic acid (C18), isostearic acid (C18), nonadecylic acid (C19), arachidic acid (C20), heneicosylic acid (C21), behenic acid (C22), tricosylic acid (C23), lignoceric acid (C24), pentacosylic acid (C25), cerotic acid (C26), heptacosylic acid (C27), montanic acid (C28), nonacocylic acid (C29), melissic acid (C30), henatriacontylic acid (C31), lacceroic acid (C32), psyllic acid (C33), geddic acid (C34), ceroplastic acid (C35) and hexatriacontylic acid (C36).

As used herein, the term "fatty acid" also includes monounsaturated fatty acids, which contain one double or triple bond in the hydrocarbon chain, and polyunsaturated fatty acids, which contain more than one double and/or triple bond in the hydrocarbon chain. Such acids include, but are not limited to the omega 3, omega 6, omega 9 fatty acids, other fatty acids such as myristoleic and palmitoleic acid and conjugated fatty acids. Examples of monounsaturated and polyunsaturated fatty acids include but are not limited to, (a) omega 3 fatty acids, such as hexadecatrienoic acid (C16:3); (by way of example, C16:3 indicates hexadecatrienoic acid has 16 carbon atoms in its hydrocarbon chain and 3 double bonds; the number of carbon atoms and double bonds in the hydrocarbon chain of other example unsaturated fatty acids is denoted in analogous fashion herein), alpha linolenic acid (C18:3) and eicosapentanoic acid (20:5), (b) omega 6 fatty acids, such as linoleic acid (18:2), docosadienoic acid (C22:2), arachidonic acid (C20:4) and tetracosatetraenoic acid (C24:5), (c) omega 9 fatty acids, such as oleic acid (C18:1), eicosenoic acid (C20:1) and nevronic acid (C24:1), and (d) conjugated fatty acids such as rumenic acid (C18:2), eleostatic acid (C18:3), and rumelenic acid (C18:3).

As used herein, the term "fatty acid" also includes branched fatty acids. Examples of branched fatty acids include, but are not limited to, monomethyl branched fatty acids, such as 14-methyl pentadecanoic acid, 6-methyl caprylic acid, 4-methyl-3-pentenoic acid, (pyroterebic acid), 2-methyl-2E-butenoic acid (tiglic acid), 2-methyl-2Z-butenoic acid (angelic acid), multimethyl branched acids, isoprenoid fatty acids (vittatalactone, all-trans-retinoic acid), branched methoxy fatty acids and hydroxy and other fatty acids such as 2-hydroxyoctanoic acid and 4-oxopentanoic acid (levulinic acid).

As used herein, the term "keto acid" refers to a fatty acid having a ketone moiety.

As used herein, the term "amino acid" refers to a fatty acid having an amine group.

As used herein, the term "derivative" has its ordinary meaning as would be understood by a person of skill in the art. With reference to a fatty acid, the term "derivative" includes, but is not limited to, a substituted fatty acid and an ester formed from the carboxylic acid group on a fatty acid. Fatty acid derivatives include, but are not limited to, methyl oleate, ethyl oleate, and methyl linoleate. Other fatty acid derivatives include, for example, glycerol monooleate.

Fatty acid derivatives also include fatty alcohols such as, for example, lauryl alcohol, stearyl alcohol, and oleyl alcohol. Oleyl alcohol is a particularly preferred fatty acid derivative.

As used herein, the term "congener" has its ordinary meaning as would be understood by a person of skill in the art, including in the present context referring to a fatty acid having the same basic molecular structure as the reference fatty acid but having a different number of substitutions or being substituted at a different position.

As used herein, the term "therapeutic agent" refers to a compound that, upon administration to a patient in a therapeutically effective amount, provides a therapeutic benefit to the patient. A therapeutic agent may be referred to herein as a drug or biologic. Those skilled in the art will appreciate that the term "therapeutic agent" is not limited to drugs or biologics that have received regulatory approval.

In the present disclosure the singular forms "a," "an," and "the" include the plural reference, and reference to a particular numerical value includes at least that particular value, unless the context clearly indicates otherwise. Thus, for example, a reference to "a therapeutic agent" is a reference to at least one of such therapeutic agents and equivalents thereof known to those skilled in the art, and so forth.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value.

In an embodiment of the invention a composition includes a first fatty acid, or derivative or congener thereof, that has a molecular structure made up of about 14 or more carbon atoms and a second fatty acid, or derivative or congener thereof, that has a molecular structure made up of about 10 or less carbon atoms. The first fatty acid may be any fatty acid having about 14 or more carbon atoms. In some embodiments the first fatty acid has about 15 or more carbon atoms and in other embodiments the first fatty acid has about 16 or more carbon atoms. In particular, the first fatty acid may be saturated, monounsaturated or polyunsaturated. The hydrocarbon chain of the first fatty acid may be straight or branched. In a preferred embodiment the first fatty acid is one or more of oleic acid, linolenic acid, linoleic acid, myristoleic acid, palmitoleic acid, or erucic acid. The second fatty acid may be any fatty acid having about 10 or less carbon atoms. In some embodiments the second fatty acid has about 9 or less carbon atoms and in other embodiments the second fatty acid has about 8 or less carbon atoms. In particular, the second fatty acid may be saturated, monounsaturated or polyunsaturated. The second fatty acid may be a keto acid or an amino acid. The hydrocarbon chain of the second fatty acid may be straight or branched. In a preferred embodiment the first fatty acid is an unsaturated fatty acid and the second fatty acid is a saturated or branched fatty acid. Preferable unsaturated fatty acids include oleic acid, linoleic acid, and linolenic acid. Preferable saturated or branched fatty acids include 2-hydroxyoctanoic acid and 4-oxopentanoic acid. In a preferred embodiment the second fatty acid is one or more of levulinic acid, 2-hydroxyoctanoic acid, 4-oxopentanoic acid, propionic acid, valeric acid, peruvic acid, acetoacetic acid, alanine, aspartic acid, asparagine, glutamic acid, glycine, lycine, or valine. In another preferred embodiment the first fatty acid is one or more of oleic acid, linolenic acid, linoleic acid, myristoleic acid, palmitoleic acid, or erucic acid and the second fatty acid is one or more of levulinic acid, propionic acid, valeric acid, peruvic acid, acetoacetic acid, alanine, aspartic acid, asparagine, glutamic acid, glycine, lycine, or valine. In a most preferred embodiment the first fatty acid is oleic acid and the second fatty acid is levulinic acid.

In another embodiment of the invention a composition includes a first fatty acid that has a molecular structure made up of about 14 or more carbons and a second fatty acid that has a molecular structure made up of about 12 or less carbon atoms. The first fatty acid may be any fatty acid having about 14 or more carbon atoms. In some embodiments the first fatty acid has about 15 or more carbon atoms and in other embodiments the first fatty acid has about 16 or more carbon atoms. In particular, the first fatty acid may be saturated, monounsaturated or polyunsaturated. The hydrocarbon chain of the first fatty acid may be straight or branched. In a preferred embodiment the first fatty acid is one or more of oleic acid, linolenic acid, linoleic acid, myristoleic acid, palmitoleic acid, or erucic acid. The second fatty acid may be any fatty acid having about 12 or less carbon atoms. In some embodiments the second fatty acid has about 11 or less carbon atoms and in other embodiments the second fatty acid has about 10 or less carbon atoms. In particular, the second fatty acid may be saturated, monounsaturated or polyunsaturated. The second fatty acid may be a keto acid or an amino acid. The hydrocarbon chain of the second fatty acid may be straight or branched. In a preferred embodiment the second fatty acid is one or more of levulinic acid, 2-hydroxyoctanoic acid, 4-oxopentanoic acid, propionic acid, valeric acid, peruvic acid, acetoacetic acid, alanine, aspartic acid, asparagine, glutamic acid, glycine, lycine, or valine. In another preferred embodiment the first fatty acid is one or more of oleic acid, linolenic acid, linoleic acid, myristoleic acid, palmitoleic acid, or erucic acid and the second fatty acid is one or more of levulinic acid, propionic acid, valeric acid, peruvic acid, acetoacetic acid, alanine, aspartic acid, asparagine, glutamic acid, glycine, lycine, or valine. In a most preferred embodiment the first fatty acid is oleic acid and the second fatty acid is levulinic acid.

Compositions of the invention including a first and a second fatty acid as described above can have amounts of first and second fatty acid that are in equal or different proportions relative to each other. The first fatty acid, and in some embodiments a derivative or congener thereof, having about 14 or more carbon atoms, can be present in the range of from about 0.1% to about 30% by weight of the total composition, or in the range of from about 1% to about 5% by weight of the total composition, or about 2.5% by weight of the total composition. In some embodiments, the composition can include any amount of first fatty acid up to an amount that is known to cause irritation in a mammal; the amount can be up to 2% by weight. The second fatty acid, and in some embodiments, derivatives or congeners thereof, having about 12 or less carbon atoms, or about 10 or less carbon atoms, can be present in the range of from about 0.1% to about 30% by weight of the total composition, or in the range of from about 1% to about 5% by weight of the total composition, or about 2.5% by weight of the total composition. The composition can include up to 25 mg of second fatty acid, and in some embodiments, derivatives or congeners thereof, per dose. The weight percent of the first fatty acid can be chosen independent of the weight percent of the second fatty acid. The composition can include a first and second fatty acid in equal proportions by weight percent, greater weight percent first fatty acid than second fatty acid, or greater weight percent second fatty acid than first fatty acid. In preferred embodiments the weight percent of the first fatty acid is greater than the weight percent of the second fatty acid, such as a composition having in the range of from about 2.5% to about 7.5% first fatty acid and having in the range of from about 0.5% to about 2.5% second fatty acid, or a composition having about 5% first fatty acid and about 1% second fatty acid. All ranges are inclusive and the maxima and minima of the specified ranges are combinable.

Compositions of the invention can have two fatty acids comprising different molecular weights as described above and one or more therapeutic agents. The invention is particularly effective with therapeutic agents that are difficult to permeate through skin or mucosal tissue. Such drugs and biologics are usually of high molecular weight, high melting point and/or their chemical structures contain one or more fused rings. Therapeutic agents having a high molecular weight include drugs and biologics having a molecular weight greater than about 300 daltons. In other embodiments therapeutic agents having a high molecular weight include drugs and biologics having a molecular weight greater than about 350 daltons or greater than about 400 daltons. Therapeutic agents having a high melting point include drugs and biologics having a melting point greater than about 200° C. In other embodiments, therapeutic agents having a high melting point include drugs and biologics having a melting point greater than about 225° C., or greater than about 250° C.

For example such therapeutic agents include, but are not limited to, hormone antagonists such as estrogens, progestins, and androgens for both male and female health, adrenocortical steroids and their synthetic analogs for inflammation and/or various manifestations of adrenal insufficiency or pituitary hormone excess, antinausea/antiemetic drugs, tricyclic antidepressants, migraine and other pain drugs including NSAIDs and narcotics, hypnotics, some beta blockers, alpha blockers, neuromuscular blocking agents, diuretics, antimalarial drugs, dermatologicals, antimetabolites, peptides such as leuprolide, goserelin or histrelin. In other embodiments the therapeutic agent may be, but is not limited to, an agent to treat Alzheimer's, an anabolic agent, an analgesic agent, an anesthetic agent, an antacid, an anti-asthmatic agent, an anticholesterolemic agent, an anti-lipid agent, an anti-coagulant, an anti-convulsant, an anti-diarrheal, an antiemetic, an anti-inflammatory agent, an antifungal agent, an anti-manic agent, an anti-migraine, an anti-nauseant, a CNS anti-depressant, an antineoplastic agent, an anti-obesity agent, an anti-Parkinson's agent, an anti-pyretic agent, an anti-spasmodic agent, an anti-thrombotic agent, an anti-uricemic agent, an anti-anginal agent, an antihistamine, an antitussive, an appetite suppressant, a biological, a cerebral dilator, a central nervous system agent, a coronary dilator, a decongestant, a diuretic, an erythropoietic agent, an expectorant, a gastrointestinal sedative, a hormone or hormone agonist or antagonist, an agent possessing mixed agonist and antagonist properties on a hormone receptor, a hyperglycemic agent, a hypoglycemic agent, a prostaglandin or prostanoid, an estrogen or anti-estrogen, a progestogen or anti-progestin, an androgen or anti-androgen, an opiate or opioid agonist or antagonist, a phenothiazine, a butyrophenone, a benzamide, a glucocorticoid, a dopamine antagonist, a hypnotic, a hypoglycemic agent, an ion exchange resin, a laxative, a mineral supplement, a mucolytic agent, a neuromuscular drug, an NSAID, an oligonucleotide, an anti- Parkinson's agent, a peptide or polypeptide, a peripheral vasodilator, a psychotropic, a polynucleotide, a sedative, a stimulant, a thyroid agent, an anti-thyroid agent, a uterine relaxant, a cervical ripening agent, an agent for the induction of labor, a vitamin, a prodrug, or an agent that promotes healing.

Specific examples of therapeutic agents suitable for use in compositions of the invention include ropinirole, pramipexole, sumatriptan, zolmitriptan, rizatriptan, almotriptan, eletriptan, naratriptan, frovatriptan, zolpidem, zaleplon, eszopiclone, ramelteon, doxepin, ketoprofen, ketorolac, piroxicam, meloxicam, diclofenac, mifepristone, ulipristal, sildenafil, vardenafil, tadalafil, alprostadil, letrozole, anastrozole, oxycodone, hydrocodone, buprenorphine, fentanyl, sufentanyl, alfentanyl, morphine, naloxone, naltrexone, leuprolide, goserelin, histrelin, pyridoxine, doxylamine, dimenhydronate, diphenhydramine, meclizine, promethazine, prochlorperazine, droperidol, metaclopramide, haloperidol, prednisone, methylprednisolone, cortisol, thyrotropin, thyrotropin-releasing hormone, estradiol, progesterone, gonadotropin-releasing hormone, gonadotropin-releasing hormone agonists or antagonists, and insulin.

Additional compounds suitable for use in compositions of the invention include estrogens, which can be useful as contraceptives and/or hormone therapies for menopause and other endocrine conditions. Suitable estrogens not mentioned elsewhere in this specification include ethinyl estradiol and estradiol-17beta.

Additional compounds suitable for use in compositions of the invention include progesterones and progestins, which can useful as contraceptives, hormone therapies, or both, for menopause and other endocrine conditions. Suitable progesterones and progestins not mentioned elsewhere in this specification include: Progesterone, Norgestimate, Norelgestromin (also called 17-deacetyl norgestimate), Norgestrel, Levo-norgestrel, Cyproterone Acetate, Gestodene, Desogestrel, Dienogest, Drosperinone, Norethindrone, and Norethindrone acetate.

Other compounds suitable for use in compositions of the invention include anti-infectives. Suitable anti-infectives not mentioned elsewhere in this specification include Fenticonazole (base, nitrate or both) and Fluconazole.

Additional compounds suitable for use in compositions of the invention include nutritional supplements and vitamins. Suitable nutritional supplements and vitamins not mentioned elsewhere in this specification include Calcium Carbonate, Cholecalciferol (a metabolite of Vitamin D), Folic Acid, Folate, and Metafolin.

Other compounds suitable for use in compositions of the invention include compounds useful for treating central nervous system (CNS) disorders. Suitable compounds useful for treating central nervous system (CNS) disorders not mentioned elsewhere in this specification include Methylphenidate (e.g., for ADHD), Paroxetine (base, mesylate salt, or both), Valproic Acid, Lithium carbonate, Fentanyl, Lidocaine, and Rivastigmine.

In preferred embodiments, a composition of the invention includes a therapeutic agent that is a serotonin receptor antagonist. Preferably, the serotonin receptor antagonist comprises a 5-HT3 receptor antagonist. Even more preferably, the serotonin receptor antagonist is selected from ondansetron, dolasetron, granisetron, tropisetron, palonosetron, or salts thereof. In a most preferred embodiment, a composition of the invention includes ondansetron (also referred to herein as "ondansetron base") or ondansetron salt. Ondansetron hydrochloride is an example of an ondansetron salt.

Compositions of the invention may be designed to be administered to the skin or mucosal tissue of a patient in need of treatment. In addition to a first fatty acid, second fatty acid, and one or more therapeutic agents as described above, compositions of the invention may also include excipients. Compositions of the invention may be formulated as gels, transdermal patches, lotions, creams, sprays, mists, emulsions, or dispersions. Appropriate excipients for formulating a gel, transdermal patch, lotion, cream, spray, or mist are readily apparent to a person of skill in the art and include, but are not limited to, stabilizers, emulsifiers, thickeners, antimicrobials, humectants, propellants, spreading agents, polymers, and adhesives, such as pressure sensitive adhesives. In particular, excipients that may be used to form a transdermal gel include, but are not limited to, alcohols, glycols, glycerin, butylated hydroxytoluene (BHT), and water.

The invention also encompasses methods of treating a patient in need thereof by administering to a patient a composition including two fatty acids comprising different molecular weights as described above and one or more therapeutic agents as described above. Methods according to the invention can be used to treat a patient with depression, Parkinson's, Alzheimer's, nausea, migraine, pain, or any combination thereof, as well as other diseases or ailments as would be understood by a person of skill in the art.

The invention also encompasses the use of compositions comprising two fatty acids each having a different molecular weight as described above, and a therapeutic agent as described above, for the manufacture of a medicant for treating a disease or condition. Such disease or condition includes depression, Parkinson's, Alzheimer's, nausea, migraine, pain, or any combination thereof, as well as other diseases or ailments as would be understood by a person of skill in the art.

EXAMPLES

The following examples, while illustrative individual embodiments, are not intended to limit the scope of the described invention, and the reader should not interpret them in this way.

Examples 1-4

Preparation of Ondansetron Transdermal Gels Without the Enhancer System of the Invention An amount of 296 grams of alcohol USP was placed in a container and 1.2 grams of ondansetron base was added and mixed until totally dissolved. Thereafter, 40 grams of propylene glycol and 40 grams of PEG 400 were added sequentially and mixed until a uniform solution was obtained. Thereafter 8 grams of Klucel HF was added with mixing until well suspended. Finally, 14.8 grams of purified water USP was added and then the total mixture was allowed to set for 24 hours until the gelling agent, Klucel HF, swelled uniformly. A clear, uniform gel was formed.

Similar gels, as above, were prepared without the enhancer system of the invention, but with the addition of different polyethylene glycols, which are components often used as solubilizers in transdermal gel systems. The preparation procedure was similar to the one presented in example 1 and the formulations themselves are shown in Table 1 below:

TABLE 1

Non-chemically enhanced formulations of Ondansetron Base

| Ingredient (grams) | Formulations | | | |
|---|---|---|---|---|
| | 1 | 2 | 3 | 4 |
| Ondansetron base | 1.2 | 1.2 | 1.2 | 1.2 |
| Alcohol USP | 296 | 296 | 296 | 296 |
| Propylene glycol | 40 | 40 | 40 | 40 |
| PEG 400 | 40 | — | — | — |
| PEG 300 | — | 40 | — | — |
| Methoxy PEG 350 | — | — | 40 | — |
| Butylene glycol | — | — | — | 40 |
| Klucel HF Pharm | 8 | 8 | 8 | 8 |
| Purified water USP | 14.8 | 14.8 | 14.8 | 14.8 |
| TOTAL (grams) | 400 | 400 | 400 | 400 |

All four formulations were clear and uniform in appearance

Example 5

Commercially Available Ondansetron Organogel (Formulation 5)

An ondansetron organogel is available from the compounding pharmacy Custom Medicine Pharmacenter. It is a complex formulation of ondansetron hydrochloride with potency of 2 mgs per 0.1 ml. It can be applied three times per day for a daily dose of 6 milligrams. It is a Pluronic Lecithin Organogel (PLO) with an aqueous phase of Poloxamer 407, potassium sorbate and water and an organic phase of lecithin, isopropyl palmitate and sorbic acid (www.plo-gel.com/Main/plo-gel.php). This commercially available formulation was obtained from the compounding pharmacy and used as the positive control in the skin diffusion studies.

Example 6

Skin Permeation Studies Using Formulations 1 Through 5 Presented in Examples 1 Through 5

Skin permeation studies were performed for the above mentioned formulations using Franz diffusion cells kept at 37° C. for the duration of the experiment. The receptor medium was phosphate buffered saline at pH 7.4, the receptor volume 12 ml and the permeation area 1.77 cm$^2$. Human cadaver skin was used and all tests were performed in triplicate. Four hundred microliters of each of the formulations was placed at the donor site of the skin diffusion cells and the experiment was initiated with the receptor medium being continuously mixed. Samples of the receptor phase were obtained at 2, 4, 8, 12, 24 and 48 hours and ondansetron concentrations were obtained using HPLC [Column-Waters C18 XBridge, 3.5 μm, 4.6 mm×150 mm, Mobile Phase-20 mM Potassium Phosphate Buffer pH 4.4 : Acetonitrile (78: 22), Flow Rate-lmL/min, Injection Volume-10 μl, Detection-216 nm, Column Temperature-40° C., Run Time-10 minutes]. The ondansetron skin flux and cumulative amount permeated after 24 hours were calculated and are shown in Table 2 below.

Figure 2:
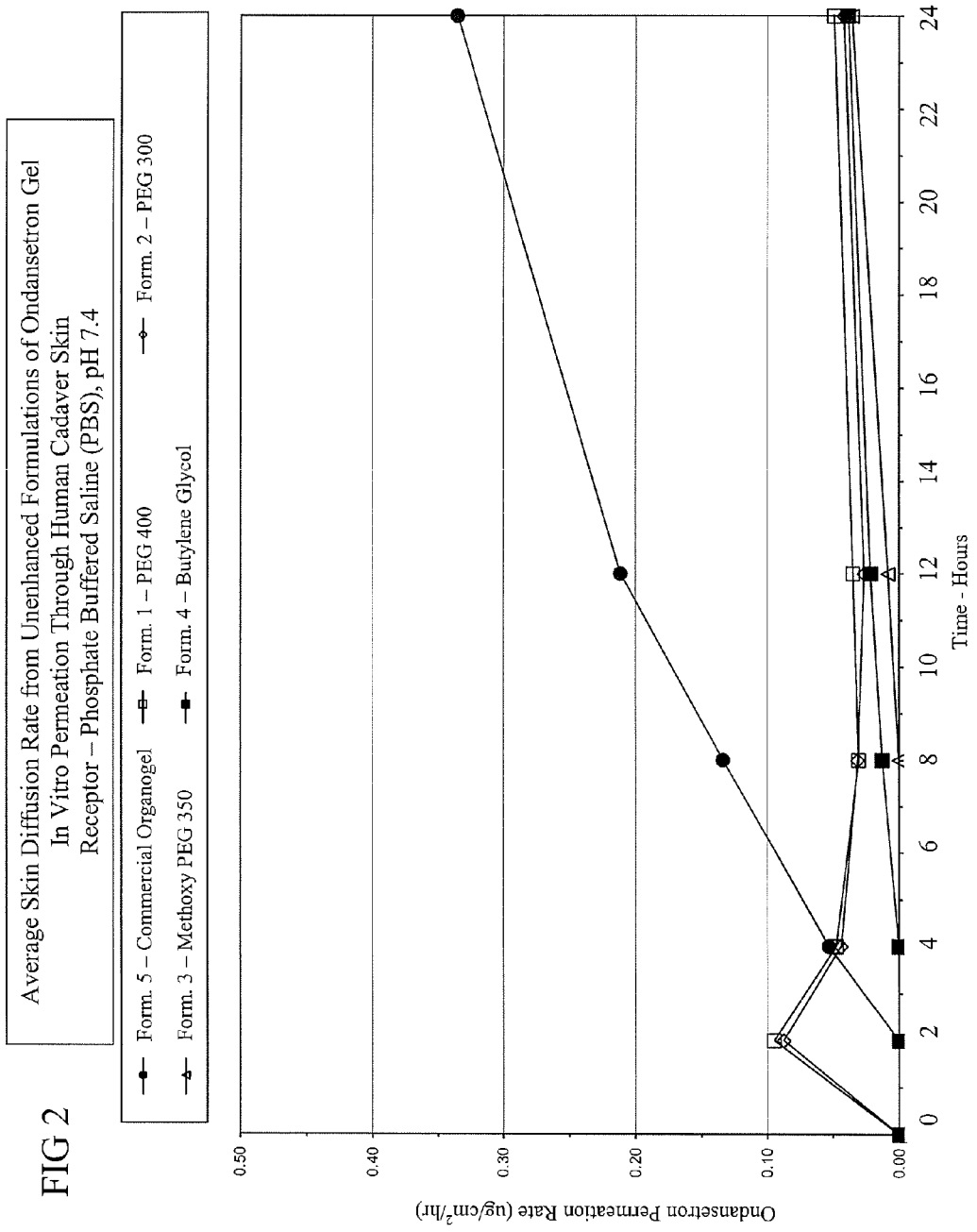
FIG. 2 illustrates average skin diffusion rate of ondansetron base that permeated through human skin over a 24 hour period without the benefit of the present invention.

FIG. 1 compares the average cumulative amount (three diffusion cells per formulation) of ondansetron base that permeated through human skin over a 24 hour period for the four formulations shown in Table 1 as well as that of the commercial organogel discussed in example 5 (formulation 5). FIG. 2 shows the average skin diffusion rate (3 diffusion cells per formulation) for the five formulations mentioned above.

TABLE 2

Flux and Cumulative Amount Of Ondansetron Permeated Through Human Cadaver Skin

| | Flux (microg/cm$^2$/hr) | Cumulative amount permeated (microg/cm$^2$) |
|---|---|---|
| Formulation 1 | 0.05 | 1.18 |
| Formulation 2 | 0.04 | 1.00 |
| Formulation 3 | 0.04 | 0.85 |
| Formulation 4 | 0.04 | 0.92 |
| Formulation 5 | 0.34 | 8.04 |

The data demonstrates that the Custom Medicine Pharmacenter's organogel is substantially better than any of the standard unenhanced formulations.

Example 7

Chemically Enhanced Formulations of Ondansetron Base

Hydroalcoholic gels similar to those described in examples 1 through 4 were prepared using chemical enhancers. The chemical enhancers used were dimethyl isosorbide, oleic acid, glycerin, levulinic acid and combinations thereof The preferred embodiment of the invention contained both oleic acid and levulinic acid. The preparation of this formulation was as follows. An amount of 294 grams of alcohol USP was placed in a container and 4 grams of ondansetron base was added and mixed until totally dissolved. Thereafter, 40 grams of propylene glycol, 20 grams of oleic acid, and 20 grams of levulinic acid were added sequentially and mixed until a uniform solution was obtained. Thereafter 8 grams of Klucel HF was added with mixing until well suspended. Finally, 12 grams of purified water USP was added and then the total mixture was allowed to set for 24 hours until the gelling agent, Klucel HF, swelled uniformly. A clear, uniform gel was formed with viscosity of 21,650 cps. All of the chemically enhanced formulations prepared and tested are shown in Table 3 below:

TABLE 3

Chemically enhanced formulations of Ondansetron Base

| Ingredient (grams) | Formulations | | | | | | |
|---|---|---|---|---|---|---|---|
| | 6 | 7 | 8 | 9 | 10 | 11 | 5 (note 1) |
| Ondansetron base | 1.2 | 1.2 | 1.2 | 4.0 | 4.0 | 4.0 | |
| Alcohol USP | 296 | 296 | 296 | 296 | 296 | 296 | |
| Propylene glycol | 40 | 40 | 40 | 40 | 40 | 40 | |
| Klucel HF Pharm | 8 | 8 | 8 | 8 | 8 | 8 | |
| Purified water USP | 14.8 | 14.8 | 14.8 | 12.0 | 12.0 | 12.0 | |
| Dimethyl Isosorbide | 40 | — | — | — | — | — | |
| Oleic acid | — | 20 | — | 40 | — | 20 | |
| Glycerin | — | 20 | 20 | — | — | — | |
| Levulinic acid | — | — | 20 | — | 40 | 20 | |
| TOTAL (grams) | 400 | 400 | 400 | 400 | 400 | 400 | |

Note 1.
Custom Medicine Pharmacenter commercial organogel formulation; exact composition not known.

Example 8

Skin Permeation Studies Using Chemically Enhanced Formulations 5 Through 11

Skin permeation studies were performed for the above mentioned formulations using Franz diffusion cells kept at 37° C. for the duration of the experiment. The receptor medium was phosphate buffered saline at pH 7.4, the receptor volume 12 ml and the permeation area 1.77 cm². Human cadaver skin was used and all tests were performed in triplicate. The results for skin flux and cumulative amount permeated through human skin was calculated for a period of 24 hours, and are shown in Table 4 below:

TABLE 4

Flux And Cumulative Amount Of Ondansetron Base Permeated Through Human Cadaver Skin

| | Flux (microg/cm²/hr) | Cumulative amount permeated (microg/cm²) |
|---|---|---|
| Formulation 5 | 0.60 | 14.3 |
| Formulation 6 | 0.04 | 1.00 |
| Formulation 7 | 1.69 | 40.6 |
| Formulation 8 | 0.00 | 0.05 |
| Formulation 9 | 2.17 | 52.0 |
| Formulation 10 | 0.08 | 1.79 |
| Formulation 11 | 18.0 | 456.0 |

The above data demonstrates that dimethyl isosorbide, levulinic acid and levulinic acid together with glycerin do not enhance the permeability of ondansetron base through human skin. Oleic acid and oleic acid in combination with glycerin appear to enhance the permeation of ondansetron base 40 to 50-fold over that of the unenhanced formulations and about 3-fold over the commercial oranogel formulation. To our great surprise oleic acid together with levulinic acid showed a tremendous increase in the permeation of ondasentron, indicating a synergistic effect between the small molecular weight (levulinic acid) fatty acid and that of the larger molecular weight (oleic acid) fatty acid. The results are even more surprising considering that levulinic acid by itself had no effect on the permeation of ondansetron through human skin. The increase in ondansetron permeation through human skin for the oleic acid/levulinic acid combination was a) 450-fold higher than that of the unenhanced formulations, b) 255-fold over the formulation containing only levulinic acid, c) 32-fold over the commercially available ondansetron oranogel and d) 9-fold over the formulation containing oleic acid.

Figure 3:
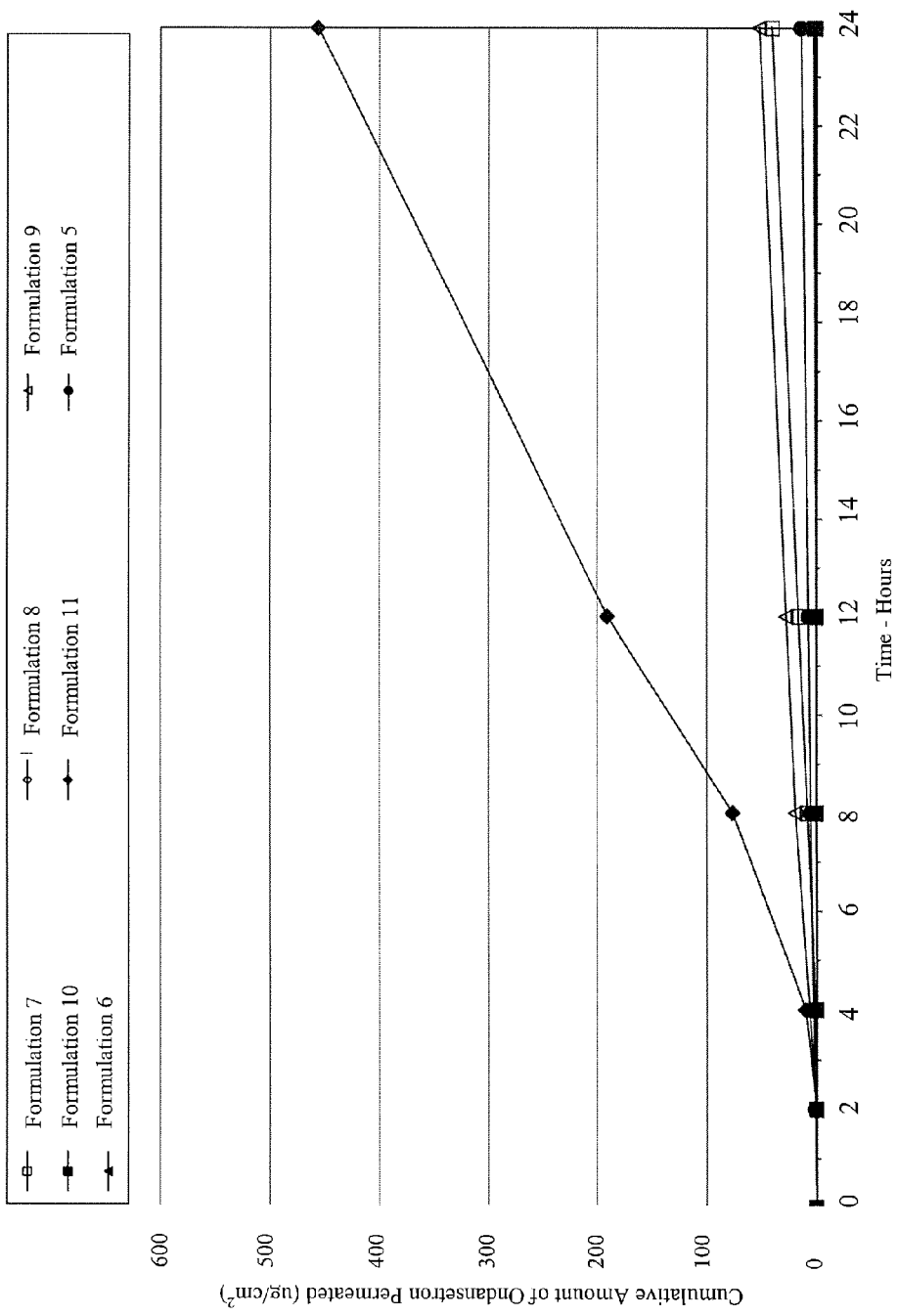
FIG. 3 illustrates average cumulative amount of ondansetron base that permeated through human skin over a 24 hour period when provided in accordance with an embodiment of the present invention.
Figure 4:
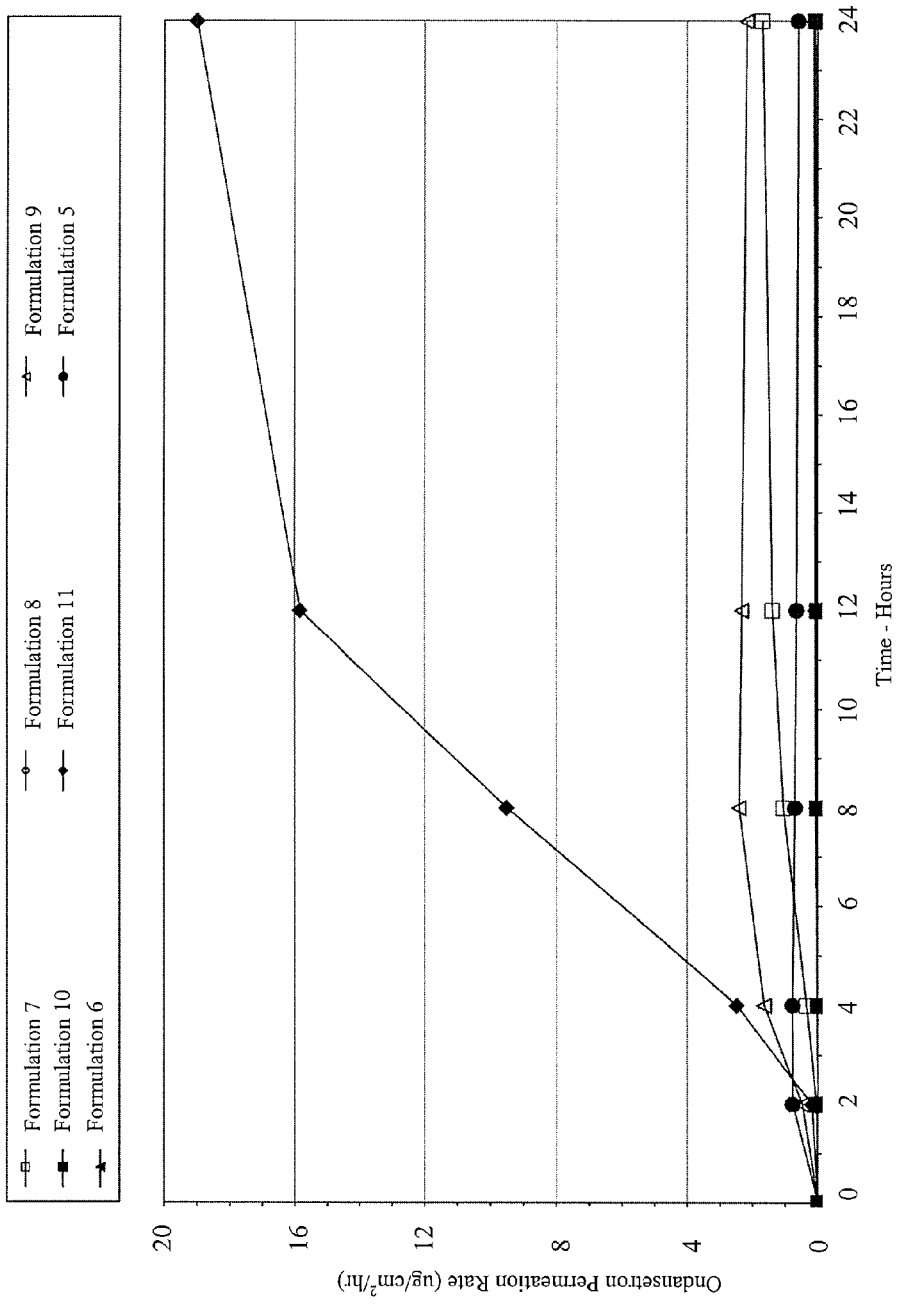
FIG. 4 illustrates average diffusion rate of ondansetron base that permeated through human skin over a 24 hour period when provided in accordance with an embodiment of the present invention.

FIG. 3 compares the average cumulative amount (three diffusion cells per formulation) of ondansetron base that permeated through human skin over a 24 hour period for five formulations, 1) the formulation of the invention containing a combination of oleic acid and levulinic acid as the enhancing system (formulation 11), 2) the formulation containing oleic acid as the enhancer (formulation 9), 3) the formulation containing levulinic acid as the enhancer (formulation 10), 4) the formulation containing no enhancer (formulation 1) and 5) the formulation of the commercially available organogel containing ondansetron. FIG. 4 shows the average skin diffusion rate (3 diffusion cells per formulation) for the five formulations mentioned above.

Example 9

Formulations for Skin Permeation Studies to Investigate the Effect of Content of Fatty Acid Enhancers and Amount of Ondansetron Base on the Skin Permeation of Ondansetron Hydroalcoholic gels similar to those described in the above examples were prepared having the formulations shown in Table 5. Human skin permeation studies were performed using these four formulations to determine the effect of a) the concentration of the skin lipid enhancing system and b) the concentration of the drug on the amount of drug that permeates through skin. In these formulations butylated hydroxytoluene (BHT) was included to protect the formulations from oxidation.

TABLE 5

Formulations Of The Invention Comprising Different Concentrations Of Fatty Acid Combination Enhancers And Drug Loadings

| | Formulations | | | | |
|---|---|---|---|---|---|
| Ingredient (grams) | 12 | 13 | 14 | 18 | 5 (note 2) |
| Ondansetron base | 3.0 | 4.5 | 3.0 | 3.0 | |
| Alcohol USP | 222 | 222 | 222 | 231 | |
| Propylene glycol | 30 | 30 | 30 | 30 | |
| Klucel HF Pharm | 6.0 | 6.0 | 6.0 | 6.0 | |
| Purified water USP | 23.7 | 7.2 | 9.0 | 21.0 | |
| Oleic acid | 7.5 | 15 | 15 | 3.0 | |
| Levulinic acid | 7.5 | 15 | 15 | 3.0 | |
| BHT | 0.3 | 0.3 | — | 3.0 | |
| TOTAL (grams) | 300 | 300 | 300 | 300 | |

Note 2.
Custom Medicine Pharmacenter commercial organogel formulation; exact composition not known.

Example 10

Skin Permeation Studies Using Enhanced Formulations of the Invention, 12 Through 14 and 18

Skin permeation studies were performed for formulations 12-14, 18, and 5 using Franz diffusion cells kept at 37° C. for the duration of the experiment. Formulation 5 representing the commercial organogel was used as the positive control. The receptor medium was phosphate buffered saline at pH 7.4, the receptor volume 12 ml and the permeation area 1.77 cm². Human cadaver skin was used and all tests were performed in triplicate. The results for skin flux and cumulative amount permeated through human skin was calculated for a period of 24 hours, and are shown in Table 6 below:

TABLE 6

Flux and Cumulative Amount Of Ondansetron Base Permeated Through Human Cadaver Skin From Formulations Of the Invention 12 through 14, and 18

| | Flux (microg/cm²/hr) | Cumulative amount permeated (microg/cm²) |
|---|---|---|
| Formulation 12 | 21.5 | 514.9 |
| Formulation 13 | 25.0 | 599.4 |
| Formulation 14 | 19.6 | 469.5 |
| Formulation 18 | 18.0 | 433.2 |
| Formulation 5 | 0.36 | 8.7 |

The above data demonstrates that a) reducing the enhancer concentration of the combination enhancing system by half or by 80% did not substantially affect the permeation of ondansetron through skin. This is important because reducing the concentration of enhancers will reduce any skin irritation caused by the enhancing system, b) increasing the concentration of the drug in the formulation, as expected, increased the skin permeation of the drug and c) the skin enhancing system of our invention provided permeation through skin which is 54 to 69-fold higher than that of the commercial organogel and d) the presence of the antioxidant BHT in the formulation does not affect the permeation of the drug through human skin.

Figure 5:
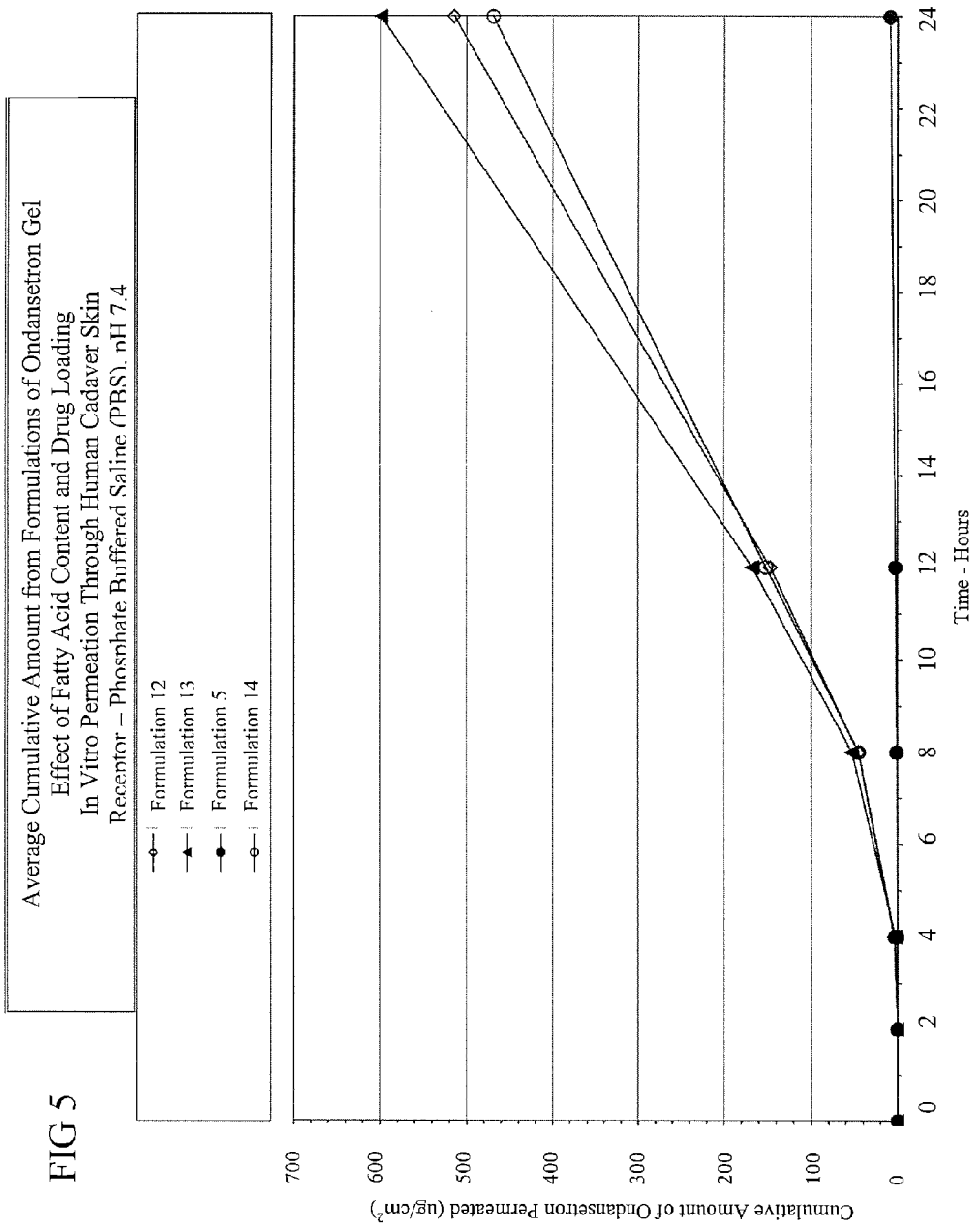
FIG. 5 illustrates average cumulative amount of ondansetron base that permeated through human skin over a 24 hour period when provided in accordance with embodiments of the present invention.
Figure 7:
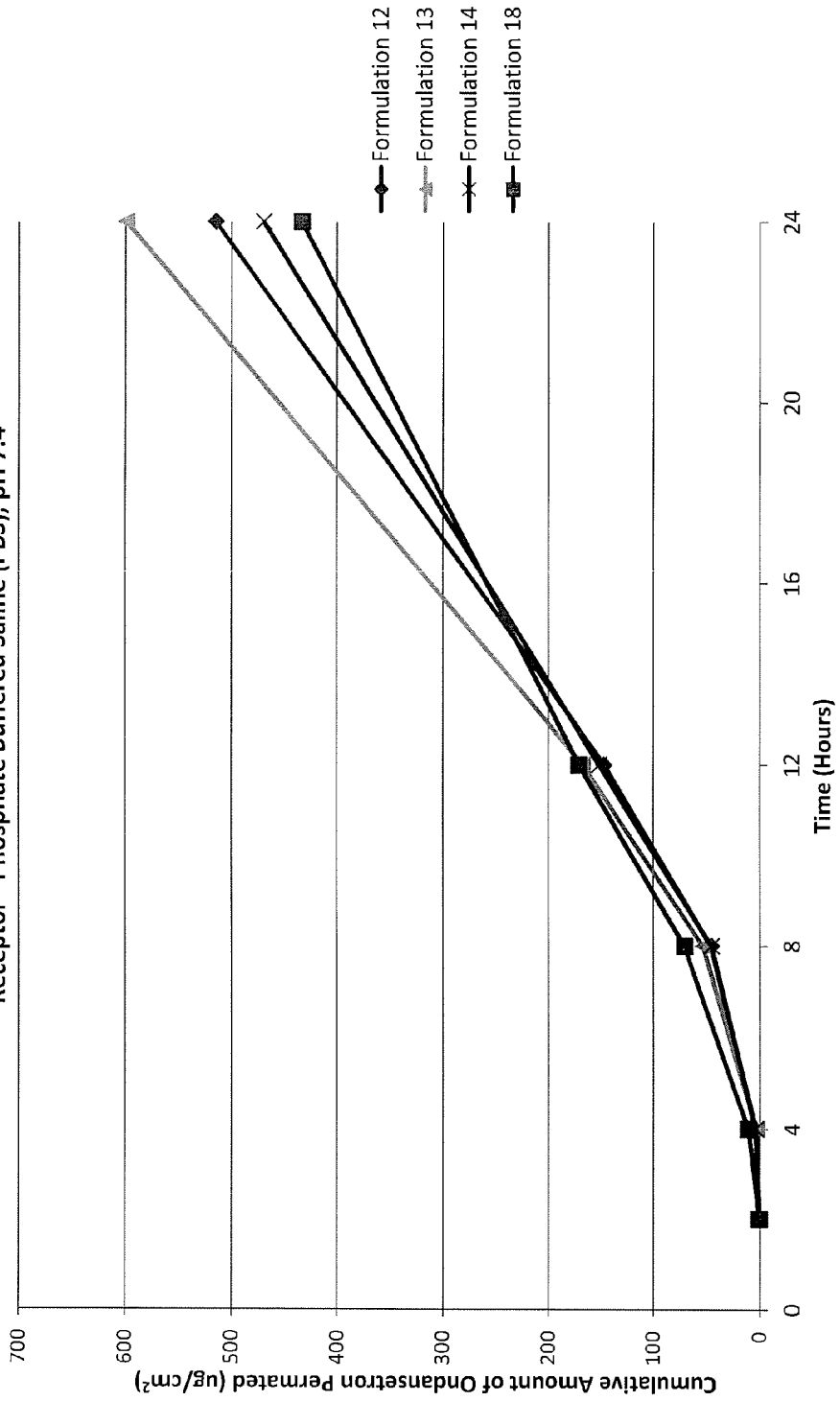
FIG. 7 illustrates average cumulative amount of ondansetron base that permeated through human skin over a 24 hour period when provided in accordance with embodiments of the present invention.
Figure 8:
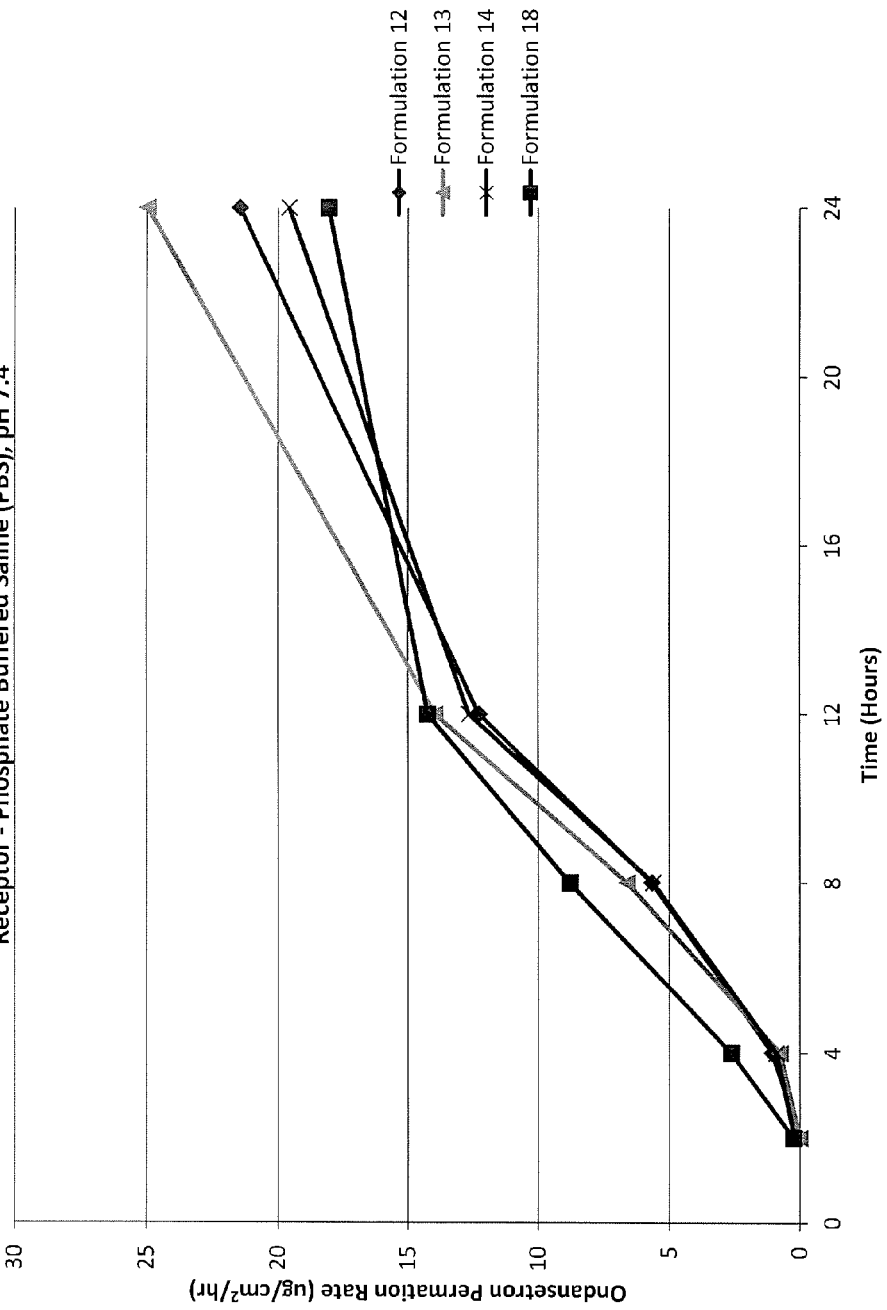
FIG. 8 illustrates average flux of ondansetron permeation through human skin in accordance with embodiments of the present invention.

FIG. 5 compares the average cumulative amount (three diffusion cells per formulation) of ondansetron base that permeated through human skin over a 24 hour period for the four formulations 12, 13, 14, and 5 of example 10. FIG. 7 compares the average cumulative amount of ondansetron that permeated through human skin over a 24 hour period for formulations 12, 13, 14, and 18 of example 10. FIG. 8 compares the average skin diffusion rate (flux) over a 24 hour period for formulations 12, 13, 14, and 18 of example 10.

Example 11

Formulations for Skin Permeation Studies to Investigate the Effect of the High Molecular Weight Fatty Acid of the Enhancer Combination on the Skin Permeation of Ondansetron Hydroalcoholic gels similar to those described in the above examples were prepared having the formulations shown in Table 7. Human skin permeation studies were performed using these three formulations to determine the effect of three different high molecular weight fatty acids of the combination enhancing system, on the permeation of ondansetron through skin. The three fatty acids were oleic acid, linoleic acid and linolenic acid.

TABLE 7

Formulations Of The Invention Comprising Different High Molecular Weight Fatty Acids, Oleic Acid, Linoleic Acid And Linolenic Acid

| | Formulations | | |
|---|---|---|---|
| Ingredient (grams) | 15 | 16 | 17 |
| Ondansetron base | 3.0 | 4.5 | 3.0 |
| Alcohol USP | 222 | 222 | 222 |
| Propylene glycol | 30 | 30 | 30 |
| Klucel HF Pharm | 6.0 | 6.0 | 6.0 |
| Purified water USP | 8.7 | 7.2 | 8.7 |
| Linoleic acid | 15 | — | — |
| Linolenic acid | — | 15 | — |
| Oleic acid | — | — | 15 |
| Levulinic acid | 15 | 15 | 15 |
| BHT | 0.3 | 0.3 | 0.3 |
| TOTAL (grams) | 300 | 300 | 300 |

Example 12

Skin Permeation Studies Using Formulations 15, 16, and 17 Comprising Different High Molecular Weight Fatty Acids in the Enhancer Combination System of the Invention Skin permeation studies were performed for formulations 15-17 using Franz diffusion cells kept at 37° C. for the duration of the experiment. The receptor medium was phosphate buffered saline at pH 7.4, the receptor volume 12 ml and the permeation area 1.77 cm². Human cadaver skin was used and all tests were performed in triplicate. The results for skin flux and cumulative amount permeated through human skin were calculated for a 24 hour period, and are shown in Table 8.

TABLE 8

Flux and Cumulative Amount Of Ondansetron Base Permeated Through Human Cadaver Skin From Formulations 15 through 17.

| | Flux (microg/cm²/hr) | Cumulative amount permeated (microg/cm²) |
|---|---|---|
| Formulation 15 | 24.3 | 583.4 |
| Formulation 16 | 24.0 | 576.5 |
| Formulation 17 | 25.0 | 599.4 |

Figure 6:
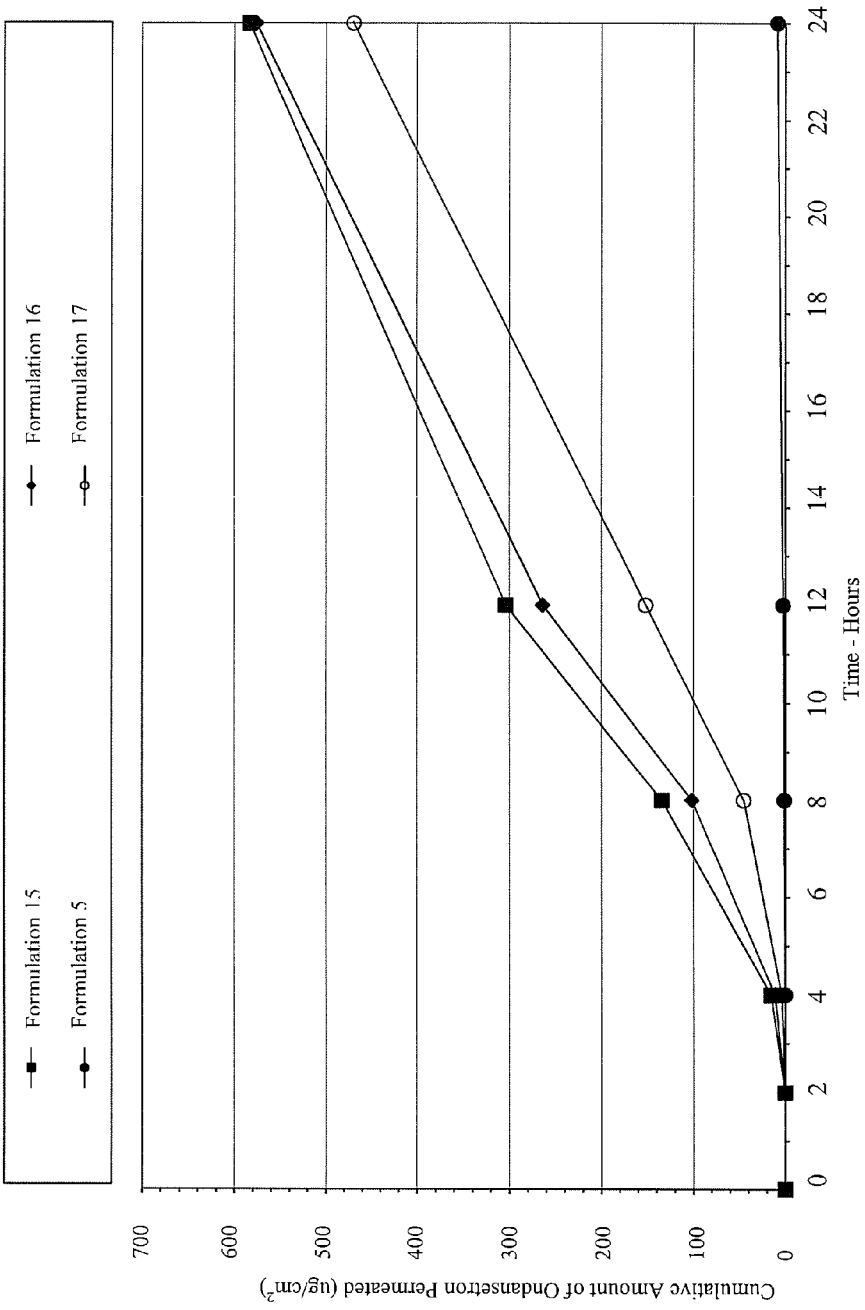
FIG. 6 illustrates average cumulative amount of ondansetron base that permeated through human skin over a 24 hour period when provided in accordance with embodiments of the present invention.

The above data demonstrates that the permeation through skin was about the same for the formulations 15-17 containing linoleic, linolenic or oleic fatty acids respectively, as the high molecular weight fatty acid in the combination enhancer system of the invention. The data supports the conclusion that the invention is broadly applicable for many different fatty acid combinations. FIG. 6 compares the average cumulative amount of ondansetron base that permeated through human skin for the three formulations 15, 16 and 17 and the commercial organogel, formulation 5.

Example 13

Finite Dose Study and Infinite Dose Study

Hydroalcoholic gels similar to those described in the above examples were prepared having the formulations shown in Table 9.

TABLE 9

Formulations of the Invention 19 and 20

| | Formulations | |
|---|---|---|
| Ingredient (grams) | 19 (Lot 121012G-A) | 20 (Lot 121012G-B) |
| Ondansetron base | 0.39 | 0.90 |
| Alcohol USP | 23.70 | 21.90 |
| Propylene glycol | 3.00 | 3.00 |
| Klucel HF Pharm | 0.60 | 0.60 |
| Purified water USP | 1.32 | 0.00 |
| Oleic acid | 0.30 | 1.50 |
| Levulinic acid | 0.30 | 1.50 |
| BHT | 0.39 | 0.60 |
| TOTAL (grams) | 30.00 | 30.00 |

Finite dose and infinite dose skin permeation studies were performed for the commercial organogel and formulations 19 and 20 using Franz diffusion cells kept at 37° C. for the duration of the experiment. The receptor medium was phosphate buffered saline at pH 7.4, the receptor volume 12 ml and the permeation area 1.77 cm². Human cadaver skin was used and all tests were performed in triplicate.

Figure 9:
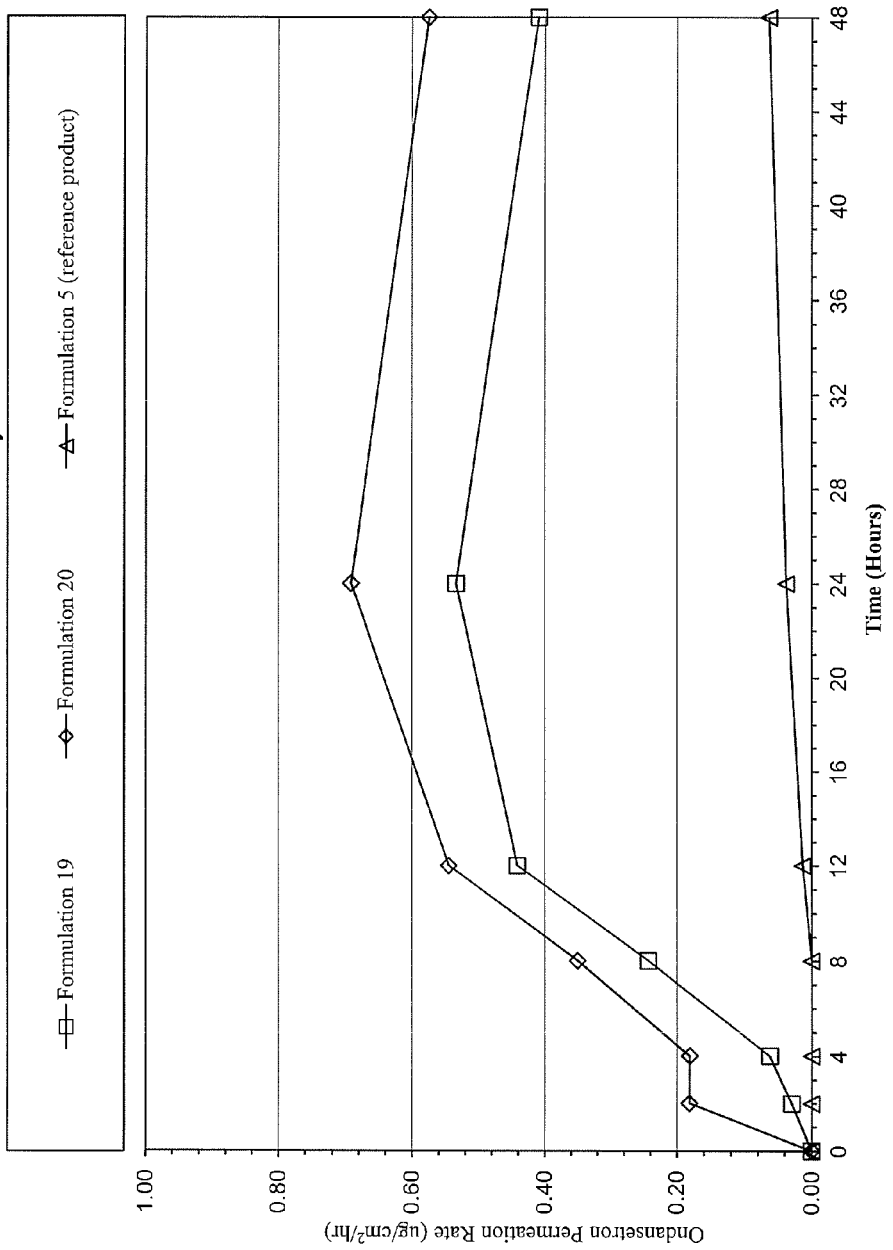
FIG. 9 illustrates average flux of ondansetron permeation through human skin in a finite dose study.
Figure 10:
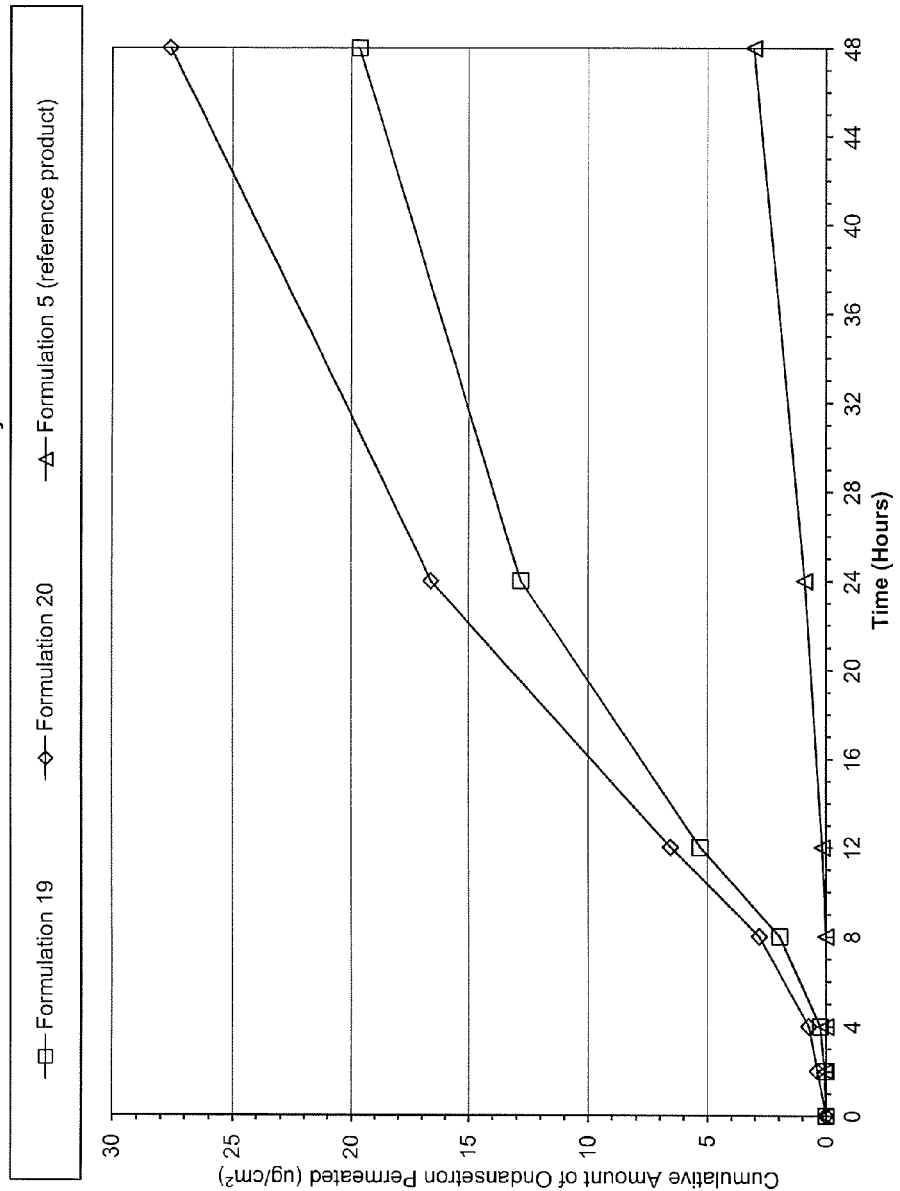
FIG. 10 illustrates average cumulative amount of ondansetron permeated through human skin in a finite dose study.

Finite dose experiments more closely simulate the transdermal application of drugs by topical means such as for gels, creams, sprays, and lotions because the amount of formulation that can be applied to skin is limited to a couple of mgs per cm². For the finite dose study, an average of 3.76 mg/1.77 cm² (2.13 mg/cm²) formulation was applied to human cadaver skin. The reference product (an ondansetron PLO gel, 2 mg/0.1 mL, described in example 5) was applied 3.85 mg/1.77 cm² (2.18 mg/cm²). The results for skin flux and cumulative amount permeated through human skin were calculated after 0, 2, 4, 8, 12, 24 and 48 hour periods, and are shown in Table 10, FIG. 9 (flux) and FIG. 10 (cumulative amount permeated) for the finite dose study.

Figure 11:
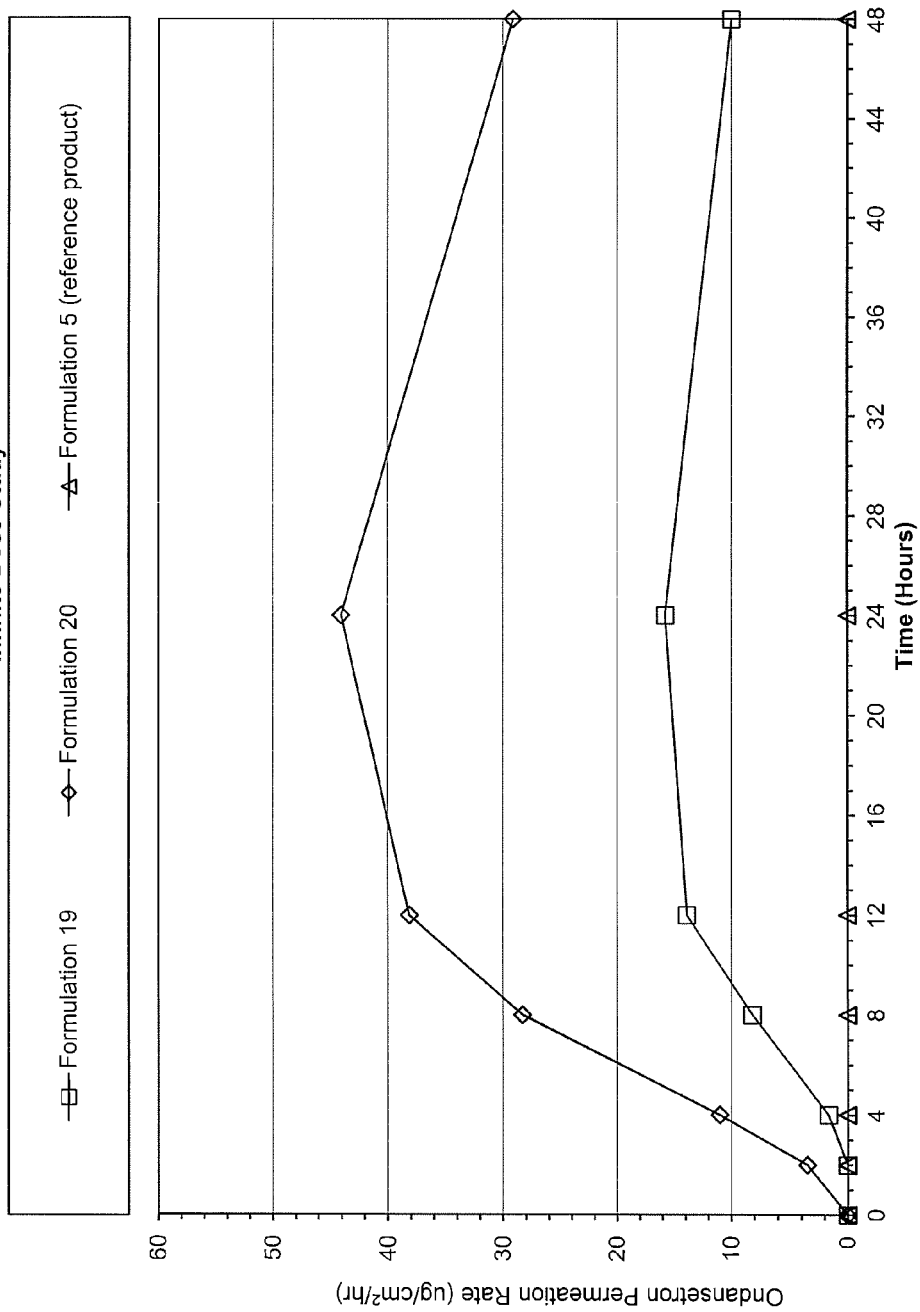
FIG. 11 illustrates average flux of ondansetron permeation through human skin in an infinite dose study.
Figure 12:
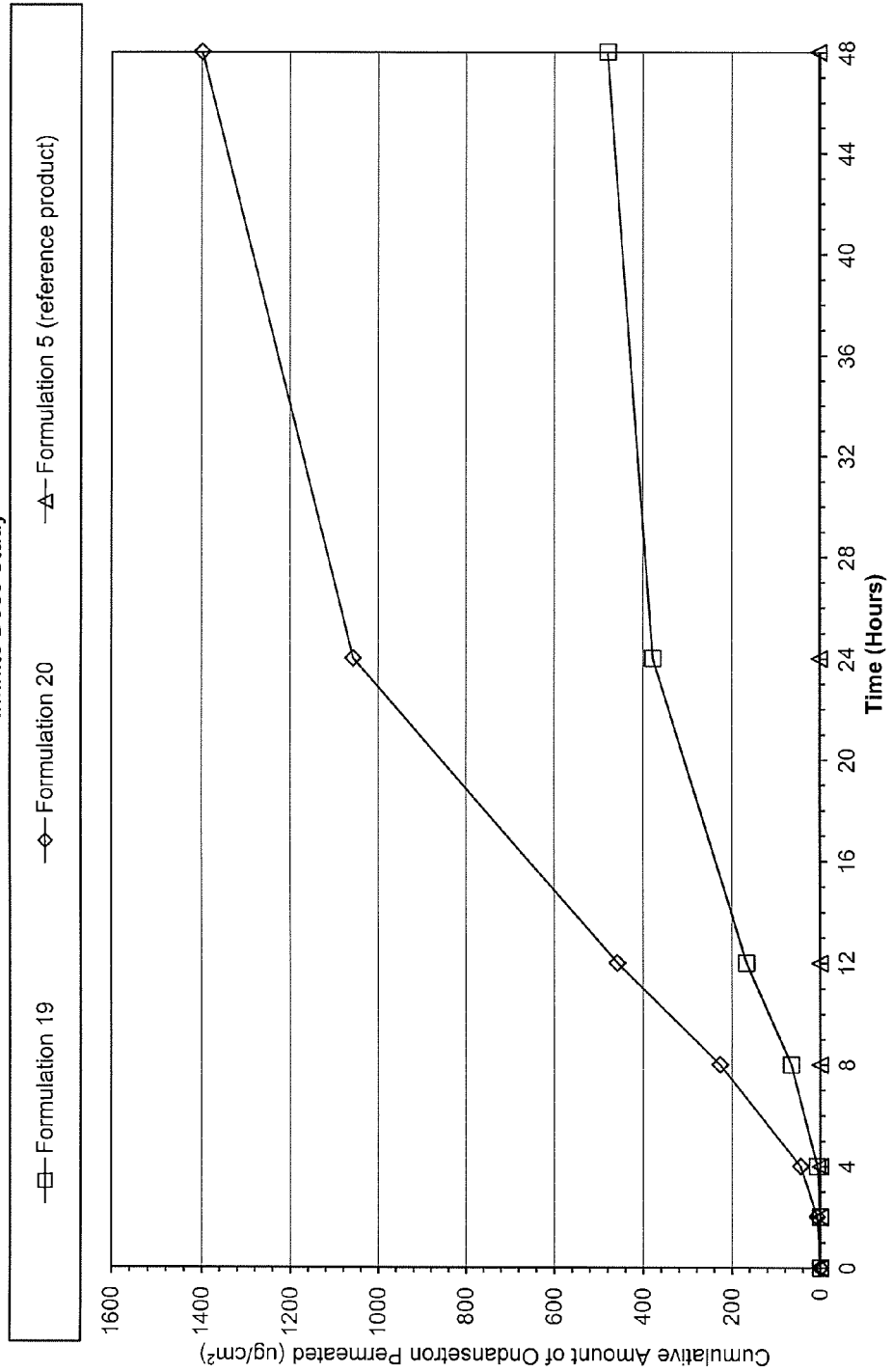
FIG. 12 illustrates average cumulative amount of ondansetron permeated through human skin in an infinite dose study.

Infinite dose experiments more closely simulate the transdermal application from patches, both matrix and reservoir, because of their ability to provide large reservoirs for drugs and enhancers per unit surface area of skin. For the infinite dose study, an average of 56.1 mg/1.77 cm$^2$ (31.7 mg/cm$^2$) formulation was applied to human cadaver skin. The reference product (an ondansetron PLO gel, 2 mg/0.1 mL, described in example 5) was applied 3.85 mg/1.77 cm$^2$ (2.18 mg/cm$^2$) on dry basis. The results for skin flux and cumulative amount permeated through human skin were calculated after 0, 2, 4, 8, 12, 24 and 48 hour periods, and are shown in Table 11, FIG. 11 (flux) and FIG. 12 (cumulative amount permeated) for the infinite dose study.

TABLE 10

Finite Dose Study - Flux and Cumulative Amount Of Ondansetron Base Permeated Through Human Cadaver Skin From Formulations 19 and 20 Compared to Ondansetron Reference Product

| | Cumulative amount permeated (microg/cm$^2$) | Flux (microg/cm$^2$/hr) |
|---|---|---|
| Formulation 19 | | |
| 0 hours | 0.000 | 0.000 |
| 2 hours | 0.058 | 0.029 |
| 4 hours | 0.247 | 0.062 |
| 8 hours | 1.94 | 0.243 |
| 12 hours | 5.29 | 0.441 |
| 24 hours | 12.8 | 0.534 |
| 48 hours | 19.6 | 0.409 |
| Formulation 20 | | |
| 0 hours | 0.000 | 0.000 |
| 2 hours | 0.363 | 0.181 |
| 4 hours | 0.723 | 0.181 |
| 8 hours | 2.80 | 0.350 |
| 12 hours | 6.54 | 0.545 |
| 24 hours | 16.59 | 0.691 |
| 48 hours | 27.58 | 0.575 |
| Ondansetron Reference Product (2 mg Ondansetron/0.1 mL) | | |
| 0 hours | 0.000 | 0.000 |
| 2 hours | 0.000 | 0.000 |
| 4 hours | 0.000 | 0.000 |
| 8 hours | 0.000 | 0.000 |
| 12 hours | 0.155 | 0.013 |
| 24 hours | 0.892 | 0.037 |
| 48 hours | 3.03 | 0.063 |

TABLE 11

Infinite Dose Study - Flux and Cumulative Amount Of Ondansetron Base Permeated Through Human Cadaver Skin From Formulations 19 and 20

| | Cumulative amount permeated (microg/cm$^2$) | Flux (microg/cm$^2$/hr) |
|---|---|---|
| Formulation 19 | | |
| 0 hours | 0.000 | 0.000 |
| 2 hours | 0.000 | 0.000 |
| 4 hours | 6.56 | 1.64 |
| 8 hours | 65.3 | 8.17 |
| 12 hours | 166.3 | 13.9 |
| 24 hours | 377.8 | 15.7 |
| 48 hours | 479.5 | 9.99 |
| Formulation 20 | | |
| 0 hours | 0.000 | 0.000 |
| 2 hours | 6.92 | 3.46 |
| 4 hours | 44.0 | 11.0 |
| 8 hours | 226.5 | 28.3 |
| 12 hours | 457.4 | 38.1 |
| 24 hours | 1056.6 | 44.0 |
| 48 hours | 1397.8 | 29.1 |
| Ondansetron Reference Product (2 mg Ondansetron/0.1 mL) | | |
| 0 hours | 0.000 | 0.000 |
| 2 hours | 0.000 | 0.000 |
| 4 hours | 0.000 | 0.000 |
| 8 hours | 0.000 | 0.000 |
| 12 hours | 0.155 | 0.013 |
| 24 hours | 0.892 | 0.037 |
| 48 hours | 3.03 | 0.063 |

Example 14

Patch Preparation

Patches incorporating the compositions of the invention can be readily prepared using methods known to those in the art. For example, the first and second fatty acids, or fatty acid derivatives, are added to a pressure sensitive adhesive solution such as, for example, Durotak™ 87-2677 (Henkel Corporation, Rocky Hill, Conn.). The therapeutic agent, such as, for example, ondansetron or ondansetron hydrochloride, is dissolved in a suitable solvent such as, for example, acetone, ethanol, or methanol, and mixed. This mixture is added to the pressure sensitive adhesive solution.

The pressure sensitive adhesive (PSA) mass is spread onto, for example, an aluminum polyester backing film to the desired thickness. One suitable backing is Scotchpak™ 9736 (3M, St. Paul, Minn.). The thickness of the mass that will be applied to the backing film can be controlled using, for example, a pilot coater such as those available from Werner Mathis USA (Concord, N.C.). The coated product is allowed to dry at, for example, 75° C. all volatile solvents are volatilized away, approximately 15 to 20 minutes. A release liner such as Scotchpak™ 9741 (3M, St. Paul, Minn.) is then applied on the PSA side of the coated mass. The resulting product is cut into individual patches of the desired size and pouched using a pouching film, for example Barex™ containing film T-1601 (American Packaging Corporation, Rochester, N.Y.).

When ranges are used herein for physical properties, such as molecular weight, or chemical properties, such as chemical formulae, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A composition for use on human skin comprising:
   a mixture comprising
   ondansetron, an ondansetron salt, or a mixture thereof;
   from about 1% to about 5% by weight of the composition of oleic acid; and
   from about 1% to about 5% by weight of the composition of levulinic acid.

2. The composition of claim 1, comprising ondansetron.

3. The composition of claim 1, comprising an ondansetron salt.

4. The composition of claim 3, wherein the ondansetron salt is ondanstron hydrochloride.

5. The composition of claim 1, comprising oleic acid.

6. The composition of claim 1 comprising ondansetron and an ondansetron salt.

7. A transdermal patch for use on human skin comprising
   a mixture comprising
   ondansetron, an ondansetron salt, or a mixture thereof;
   from about 1% to about 5% by weight of the mixture of oleic acid; and
   from about 1% to about 5% by weight of the mixture of levulinic acid.

8. The transdermal patch of claim 7, comprising ondansetron.

9. The transdermal patch of claim 7, comprising an ondansetron salt.

10. The transdermal patch of claim 9, wherein the ondansetron salt is ondanstron hydrochloride.

11. The transdermal patch of claim 7 comprising ondansetron and an ondansetron salt.

* * * * *